United States Patent [19]

Duncan

[11] Patent Number: 5,055,051

[45] Date of Patent: Oct. 8, 1991

[54] SEMI-ANTHROPOMORPHIC BILIARY/RENAL TRAINING PHANTOM FOR MEDICAL IMAGING AND LITHOTRIPSY TRAINING

[75] Inventor: William J. Duncan, Roswell, Ga.

[73] Assignee: Dornier Medical Systems, Inc., Marietta, Ga.

[21] Appl. No.: 561,885

[22] Filed: Aug. 3, 1990

[51] Int. Cl.$^5$ .................. G09B 23/30; G09B 23/28; G09B 23/00; A61B 5/06
[52] U.S. Cl. .................. 434/262; 434/267; 434/272
[58] Field of Search ............... 434/262, 267, 272, 269, 434/218; 604/256; 128/24 EL; 264/222

[56] References Cited

U.S. PATENT DOCUMENTS

| | | |
|---|---|---|
| 2,324,702 | 7/1943 | Hoffmann et al. |
| 4,286,168 | 8/1981 | Carr. |
| 4,286,455 | 9/1981 | Ophir et al. |
| 4,493,653 | 1/1985 | Robbins et al. |
| 4,669,472 | 6/1987 | Eisenmenger ............ 128/24 EL |
| 4,807,626 | 2/1989 | McGirr ................. 606/127 |

FOREIGN PATENT DOCUMENTS

| | | | |
|---|---|---|---|
| 402070 | 4/1974 | U.S.S.R. ............ | 434/218 |
| 2799 | of 1906 | United Kingdom ...... | 604/256 |

OTHER PUBLICATIONS

"Application of Hydroelastic Waves to the Removal of Small Gallstones"; Y. P. Wu et al; Journal of Biomechanical Engineering; May 1981, vol. 103, No. 2, pp. 79-82.
Article by Madsen et al. entitled "An Anthropomorphic Torso Section Phantom for Ultrasonic Imaging", Med. Phys. 7(1), Jan./Feb. 1980 (1980 Am. Assoc. Phys. Med.), pp. 43 to 50.

Primary Examiner—Richard J. Apley
Assistant Examiner—Karen G. Horowitz
Attorney, Agent, or Firm—Jones, Askew & Lunsford

[57] ABSTRACT

An apparatus and method for training physicians and technicians to locate stones found in simulated human body organs, principally simulated biliary and renal calculi, and then actually fragment these calculi using ESWL. A reusable semi-anthropomorphic phantom comprises an opaque liver tissue-equivalent mass having anatomically correct simulated organ cavities associated with the midsection of a human body, principally the gall bladder and the kidney. Channels lead from the exterior of the phantom to the simulated organs. A concrement is introduced into at least one simulated organ, the channels and simulated organs are filled with a fluid-like substance, and the channels are closed with plugs. A trainee then utilizes an ultrasound or X-ray locating device to examine the phantom until the concrements are located. The coordinates of the located concrements are then utilized with a concrement destroying apparatus such as an extracorporeal shock wave lithotripter (ESWL). The trainee then focuses the energy of the concrement destroying apparatus (such as a shock wave) towards the located concrements, thereby causing fragmentation. The channels can then be opened and the contents of the simulated organ removed to inspect the results of the procedure.

30 Claims, 3 Drawing Sheets

SEMI-ANTHROPOMORPHIC BILIARY/RENAL TRAINING PHANTOM FOR MEDICAL IMAGING AND LITHOTRIPSY TRAINING

TECHNICAL FIELD

The present invention relates generally to medical imaging and extracorporeal shock wave lithotripsy ("ESWL"), and more particularly relates to a novel phantom and method for training technicians and physicians in the ultrasonic or X-ray location and ESWL destruction of biliary and renal calculi within a simulated gall bladder or kidney.

BACKGROUND OF THE INVENTION

Substantial numbers of people are diagnosed every year with kidney stones and gall stones, termed renal and biliary calculi. Heretofore, painful surgery or lengthy drug therapy were the only known methods of treating such calculi. Recently, ESWL has become an accepted method of noninvasively treating human calculi.

The ESWL procedure used to fragment kidney stones and gall stones is well known. An ultrasonic or X-ray locating device is employed to pinpoint the exact location of a calculus found in the kidney or gall bladder. After the stone is located, a physician or technician trained in the use of an ESWL apparatus focuses the shock wave of the apparatus at the calculus and triggers a focussed shock wave. The calculus is destroyed by fragmentation in response to the shock wave, and the particles of the calculus, being substantially reduced in size, are typically passed through the bile ducts or urethra without substantial harm or pain.

It is extremely important that the physician or technician be able to accurately locate a calculus and correctly focus the shock wave on a located calculus. If the shock waves are not focussed correctly, complications can arise such as damage to other tissues or organs in the patient's body, and the need for application of additional shock wave therapy (which is not a completely painless procedure) to complete the destruction of the calculus. Therefore, there is a need for efficient and accurate tools for training physicians and technicians in the location of calculi, ESWL focussing, and application of an ESWL shock wave to the located calculi in a harmless training environment, to facilitate the efficient and safe location of gall stones and kidney stones in live patients with reduced risk of error and harm to the patient, or without excessive application of shock wave therapy.

One known device used for training technicians in ultrasound techniques is described in the article entitled "Anthropomorphic Torso Section Phantom for Ultrasonic Imaging" by Madsen et al. This article describes a torso section phantom for use as a training aid for ultrasonic technicians or as a tool in the development of more sophisticated ultrasound scanners. The Madsen et al. phantom comprises a tissue equivalent kidney, a tissue equivalent fat pad surrounding the kidney, a tissue equivalent aorta, tissue equivalent tumors, bowel gas, ribs, a spine, and resolution fibers. The remainder of the phantom is filled with a tissue equivalent liver material. All tissue types represented in the phantom are mimicked with respect to the attenuation coefficient, density, and the speed of sound. The tissue equivalent aortic blood, cysts, and tumors are molded around stainless steel wire and suspended in the phantom before the tissue equivalent liver material is poured. After the tissue equivalent liver material is poured and congealed, the suspending wires are withdrawn, thereby forming voids representing blood, cysts, and tumors in the phantom.

It was a requirement of the Madsen et al. phantom that the shape of the objects possess considerable geometric simplicity, mainly for the purpose of demonstrating and explaining scanning artifacts related either to discontinuities in density and/or speed of sound at smooth organ boundaries or to variations in the average speed of sound over pulse echo paths. Thus, none of the organs or shapes within this phantom are constructed to anatomically exactly resemble their human counterparts. Nor is any means provided for introducing a real or simulated calculus into a simulated organ for imaging. Consequently, an ultrasound technician will not see the actual shape of organs or calculi found in the human body when viewing the interior of the phantom.

Moreover, the Madsen et al. phantom is not constructed of a material suitable for being subjected to repetitive shock wave impulses, nor is it constructed in a manner so as to allow placement of calculi for location and actual destruction using ESWL. Because of these and other limitations, the Madsen et al. phantom is not suitable for use as a teaching and training aid for ultrasonic location and ESWL destruction of renal and biliary calculi.

Another phantom is described in U.S. Pat. No. 4,493,653 to Robbins. This patent describes a biopsiable ultrasound phantom for training technicians to ultrasonically locate a cyst, then perform an actual biopsy on the located cyst in the phantom. A plurality of small balloons filled with a viscous substance are provided for mimicking cysts. The balloons are suspended with nylon threads and then hung in a box. The box is then filled with a gelatinous substance comprising tissue eqivalent material. After the material has set, an ultrasonic scanner is placed against the top surface of the phantom and a technician locates a "cyst". Using the image provided by the ultrasonic scanner, the technician guides a biopsy needle into the located cyst, then aspirates the viscous substance from the cyst.

However, the Robbins phantom is also not an effective teaching and training aid for the ultrasonic location of calculi and simulated ESWL application because it has a finite number of cysts. No means are provided for introducing a calculus. When all the cysts have been aspirated, the usefulness of this phantom has ended and a new phantom must be constructed. Moreover, each of the plurality of cysts is the same, and the phantom is not constructed anthropomorphically so that the ultrasonic images substantially comport with the appearance of an actual human patient.

There is accordingly a need for a method and apparatus which can train physicians and technicians in the combination of medical imaging and ESWL techniques. There is also a need for an apparatus which can duplicate the size, shape and position of organs found within the human body. There is a further need for an ultrasound and ESWL training and teaching apparatus which can be used an inexhaustible number of times.

SUMMARY OF THE INVENTION

Briefly described, the present invention provides an apparatus and method for training doctors and technicians to locate stones found in simulated human body organs with an imaging device such as an ultrasonic imaging apparatus, principally simulated biliary and renal calculi, and then actually fragment these calculi using ESWL. Gall stones and or kidney stones, generally referred to as concrements or calculi, are placed in a semi-anthropomorphic phantom which anatomically simulates organs located in the midsection of the human body, especially the gall bladder, common bile duct, cystic duct, and the kidney. A trainee then utilizes a locating device to examine the phantom until the concrements are located. The coordinates of the located concrements are then entered into a concrement destroying apparatus such as an extracorporeal shock wave lithotripter (ESWL). The trainee then focuses the energy of the concrement destroying apparatus, such as a shock wave, towards one of the located concrements, thereby causing fragmentation.

More particularly described, the preferred embodiment of the present invention comprises a phantom that is ellipsoid in shape and filled with a tissue equivalent material that has the same attenuation coefficient and speed of sound as human liver. The phantom includes at least one organ-simulating cavity molded to mimic the size and shape of a concrement-accumulating organ such as a kidney or gall bladder, or the common and cystic ducts. In the preferred embodiment, two simulated organs are provided, one simulating a kidney and one simulating a gall bladder. The placement of the simulated organ(s) in the phantom matches the position and orientation of the corresponding organ in the human body.

At least one channel extends downwards from a lateral outer surface of the phantom into the interior of the phantom, the channel leading to the simulated organ. In the preferred embodiment, three channels are provided, one leading to a simulated gall bladder, another channel leading to a simulated kidney, and the third leading to the common bile duct. A fluid fills the channels and the simulated organs. A plug or stopper is then placed into the openings of the channel, thereby trapping the fluid within the phantom and simulated organ, and lending further realism to images generated by the locating device.

More particularly describing the preferred method for locating and fragmenting calculi such as gall stones and kidney stones found in the human body, simulated concrements or calculi are inserted into the simulated organ by introducing through the channels leading to the simulated organ. The channel and simulated organ are then filled with fluid. The trainee applies ultrasound coupling jelly on the exterior shaped surface of the phantom, at a point corresponding to the abdominal side where lower abdominal ultrasonic imaging is customarily applied. An ultrasound transducer is then guided over the exterior of the phantom in the jelly-coated area. The technician moves the ultrasound transducer, viewing the ultrasonic images, until at least one concrement is located within the phantom and identified as such. In integrated systems which incorporate a combined ultrasonic locating device and ESWL system, the coordinates of the identified concrement are then automatically entered into the ESWL aiming subsystem. For other systems, the trainee enters the coordinates into a concrement destroying apparatus.

The trainee then aims the shock wave of the ESWL apparatus or other concrement destroying apparatus at the calculus, and enables the system to destroy the concrement. The shock wave, if aimed correctly, will cause the calculus to fragment into many smaller pieces, in the manner of an actual renal or biliary calculus. After all calculi have been located and fragmented, the plugs are removed from the phantom. The phantom is inverted, and the fragmented calculi and fluid exit the phantom, thereby allowing inspection of the results of the procedure.

After a new concrement or calculus is introduced through the channel into the simulated organ and filled with new fluid, the phantom will be ready for another teaching and training session.

Accordingly, it is an object of the present invention to provide an improved method and apparatus for training physicians and technicians in medical imaging and ESWL techniques.

It is another object of the present invention to provide a reusable ESWL training phantom which allows in vitro location and destruction of actual concrements.

It is also an object of the present invention to provide an improved method and apparatus for training physicians and technicians to ultrasonically locate concrements found in the gall bladder and kidneys then fragment these concrements using an ESWL.

It is another object of the present invention to provide an apparatus which anatomically duplicates the size, shape and placement of organs found in the midsection of the human body so as to provide a realistic ultrasonic or X-ray image in an medical imaging and concrement locating device.

It is another object of the present invention to provide an apparatus which can be used repeatedly for training physicians and technicians in ultrasound location and ESWL treatment techniques without exhausting a limited preexisting supply of simulated concrements or other objects.

It is another object of the present invention to provide an improved ultrasound training phantom for allowing the insertion of simulated concrements into a simulated kidney, a simulated gall bladder, or a simulated cystic or common bile duct, location of such concrements with an existing ultrasonic locating device, actual shock wave treatment of the located concrements with an ESWL apparatus, and retrieval of the fragmented concrements for inspection after application of the shock waves.

These and other objects, features, and advantages of the present invention may be clearly understood and appreciated from a review of the following detailed description of the disclosed embodiments and by reference to the appended drawings and claims.

DETAILED DESCRIPTION OF THE DISCLOSED EMBODIMENTS

Figure 1:
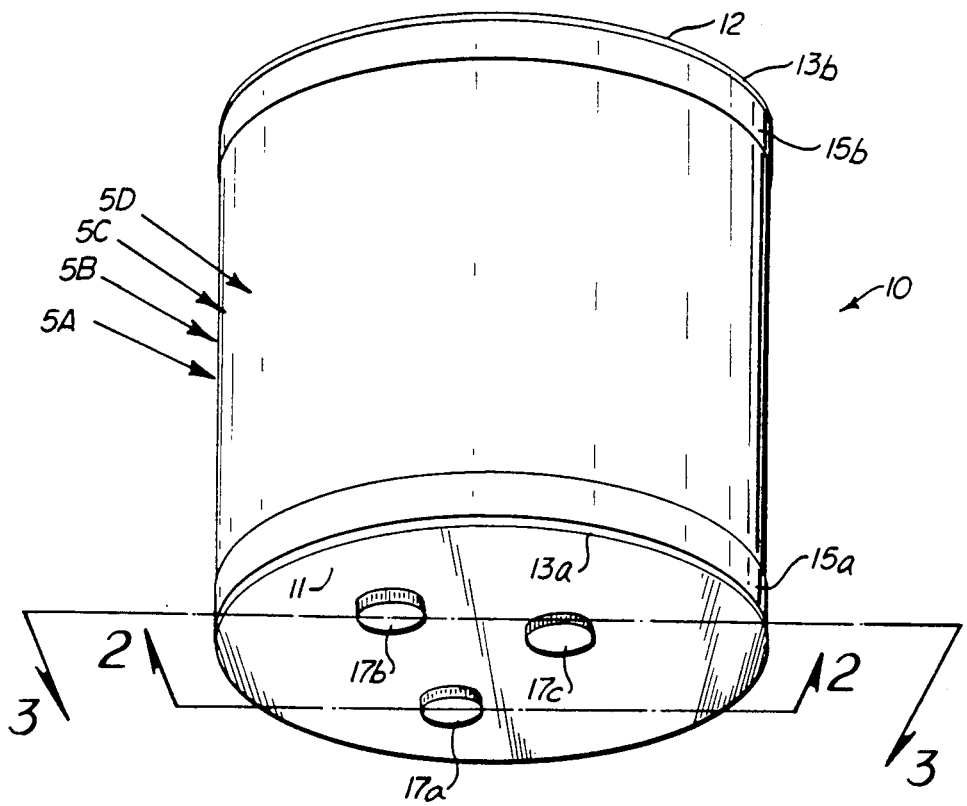
FIG. 1 is a perspective view of the preferred embodiment of a semi-anthropomorphic training phantom embodying the present invention.

Referring now to the drawings, in which like numerals indicate like elements throughout several views, FIG. 1 illustrates a semi-anthropomorphic training phantom 10 constructed in accordance with the present invention. The phantom 10 is generally ellipsoid in shape with a flat bottom portion 11 and flat top portion 12, having dimensions of about 16 cm by about 34 cm. The ellipsoid shape simulates the size and shape of a section of the lower abdomen of an average-sized human being. The preferred height of the phantom is about 27-30 cm. Plates 13a and 13b, preferably approximately 0.5 inches in width and made of a suitable rigid material such as Lucite or other plastic, are affixed to the bottom portion 11 and top portion 12, respectively, of the phantom 10, to provide for lateral stability and rigidity and facilitate movement and handling.

The phantom 10 further comprises two ellipsoidal collars 15a and 15b, made of Lucite or other suitable plastic material, preferably at least about 2 centimeters in width, to provide protection against tearing. With the collars 15, the scannable height of the phantom 10 is at least about 23-26 cm. The collar 15a is affixed below the bottom portion 11 of the phantom 10. Similarly, the collar 15b is affixed above the top portion 12 of the phantom 10.

Located on the bottom portion 11 of the phantom 10 are three ports 16a, 16b, 16c. Ports 16a-16c provide access into the interior of the phantom 10, and specifically into simulated organs. Plugs 17a, 17b, 17c fit securely into ports 16a, 16b, 16c, respectively, thereby sealing off the interior of the phantom 10.

Figure 2:
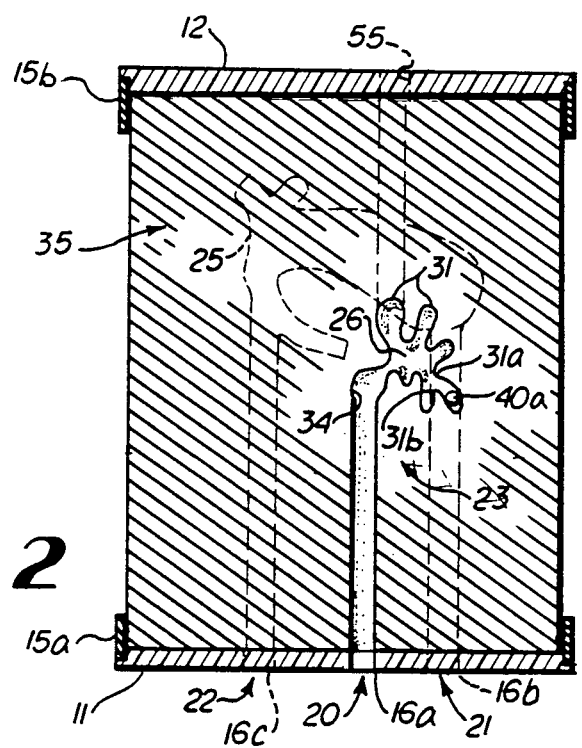
FIG. 2 is a cross sectional view of the preferred embodiment of the interior of the phantom shown in FIG. 1, taken along the line 2—2.
Figure 3:
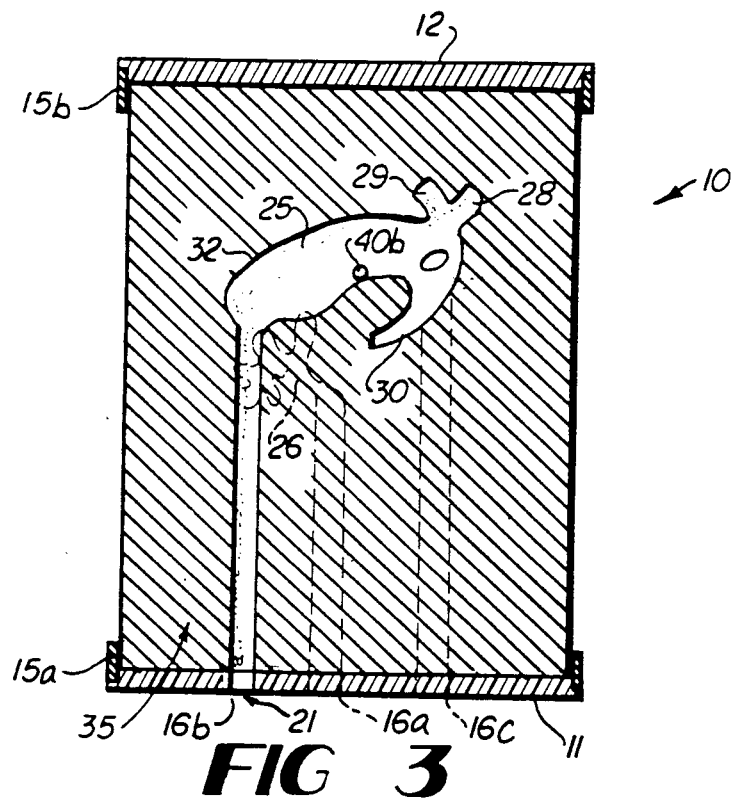
FIG. 3 is a cross sectional view of the preferred embodiment of the interior of the phantom shown in FIG. 1, taken along the line 3—3.

FIGS. 2 and 3 provide sectional views of the interior of the phantom 10. Three channels 20, 21, 22 extend upwardly from the ports 16a, 16b, 16c, respectively into the interior 23 of the phantom 10. The channel 20 leads to a simulated kidney, the channel 21 leads to a simulated gall bladder, and the channel 22 leads to a simulated common bile duct. Cavities 25, 26, 28, 29, 30 are formed in the interior of the phantom 10 which closely resemble in size, shape and position of various organs and ducts found in the human body.

Inasmuch as a primary object of the present invention is to provide for training in the location and destruction of calculi, the organs preferably simulate concrement-accumulating organs and ducts such as the gall bladder, kidney, or common bile duct. Thus, in the preferred embodiment a gall bladder cavity 25, a kidney cavity 26, a hepatic duct 28, a cystic duct 29, and a common bile duct cavity 30 are formed in the interior of the phantom 10. The organ and duct cavities 25-30 are positioned somewhat offset from the center of the mass of material forming the phantom 10, displaced relative to each other and relative to the outer surfaces of the phantom in the manner of the corresponding actual human organs.

Figure 4:
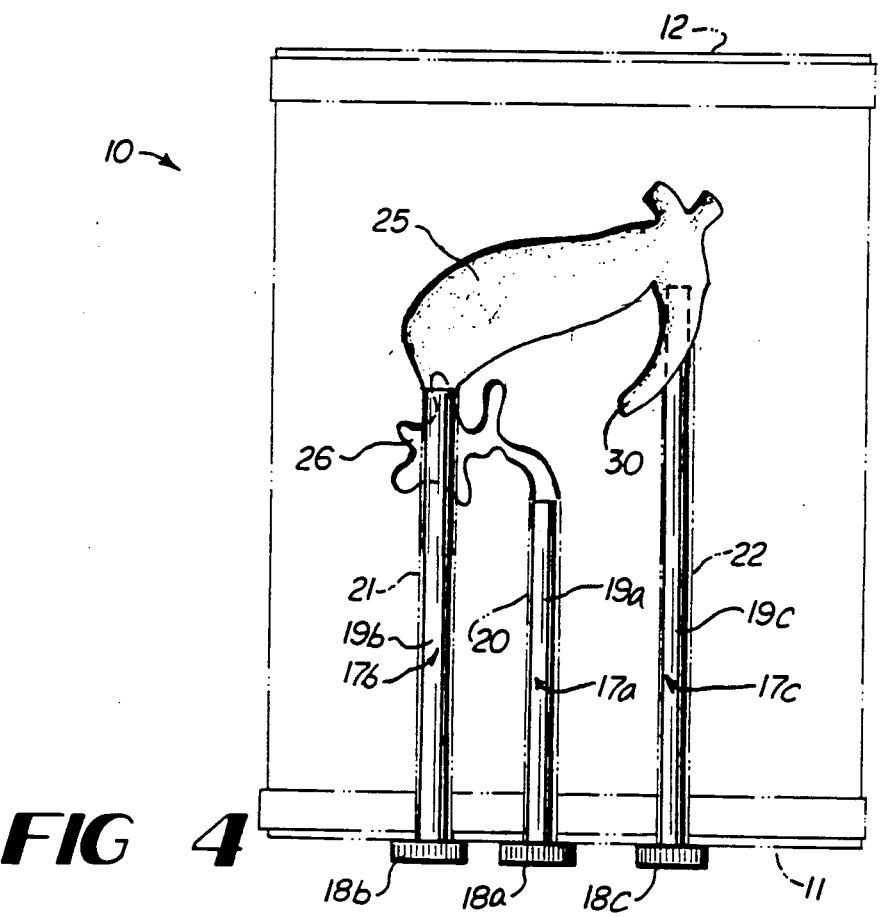
FIG. 4 is an anterior projection view of the preferred phantom shown in FIG. 1.

As best seen in FIG. 4, each of the plugs 17a-17c comprises a plug cap 18 which fits adjacent the outer surface of the bottom portion 11 when the plug is in place, and an elongate cylindrical portion 19 which fits securely in its respective channel 20, 21, 22 and extends from the outer surface of the bottom portion 11 to the beginning of an organ or duct cavity. Each of the cylindrical portions 19 are of different lengths so as to terminate at the beginning of its respective organ or duct cavity. For example, the plug 17a for the kidney channel 20 includes an elongate portion 19a which extends to the beginning of the kidney cavity 26.

The plugs 17 in the disclosed embodiment are made of nylon or Teflon. Since the plugs 17 are made of a material different from that of the phantom, an acoustic shadow may be formed in the image, this shadow does not adversely affect the operation and effectiveness of the invention.

Referring now to FIG. 2, the channel 20 preferably enters the simulated kidney cavity 26 near the fundus 34 of the simulated kidney cavity 26, so as to allow the ultrasonic image of the simulated kidney to be as accurate as possible, while still allowing adequate access to the simulated organ for placement of concrements such as 40a. The gall bladder cavity 25, being in front of the kidney cavity 26, is shown in phantom in FIG. 2.

Referring now to FIG. 3, the gall bladder cavity 25 is formed at the end of the channel 21 and the kidney cavity 26 is formed at the end of the channel 20, and a common bile duct 30 is formed at the end of the channel 22.

It will be appreciated that channels 20 and 21 can terminate anywhere in the simulated organ cavities 25, 26, but it is believed that an entry point of the channel 21 into the gall bladder cavity 25 at the top 32 of the bladder provides a more realistic simulation inasmuch as a simulated concrement such as shown at 40b will tend to settle to the bottom of the cavity. On the other hand, the channel 20 leading to the kidney cavity 26 preferably enters the cavity near the fundus 34 of the simulated kidney.

The gall bladder cavity 25 is also preferably formed with a simulated hepatic duct 28, a simulated cystic duct 29 and a simulated bile duct 30, for more realistic imaging. The channel 22 preferably leads to a simulated portion of the simulated bile duct 30, so that concrements in the bile duct can be imaged and treated.

Calyces 31 are preferably formed on the interior of the kidney cavity 26. As shown in FIG. 2, a stone 40a can be lodged between calyces such as 31a, 31b so as to more accurately simulate a real life situation.

Figure 6:
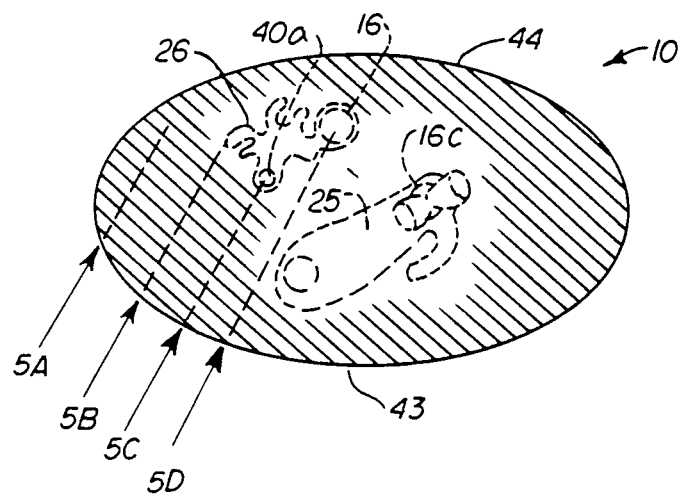
FIG. 6 is a top plan view of the preferred embodiment of the phantom shown in FIG. 1.

As will be seen best in FIG. 6, viewing the phantom 10 from the front 43, the gall bladder cavity 25 is preferably placed in front of the kidney cavity 26 so as to emulate the position of the two organs in the midsection of the human body. The gall bladder cavity 25 and the kidney cavity 26 are formed to be approximately the same size and shape as their human counterparts and will be recognized as such when a physician or technician is scanning the phantom 10 with an ultrasound device.

Surrounding the gall bladder cavity 25 and the kidney cavity 26 is a congealed tissue equivalent material 35. Preferably, the tissue equivalent material 35 has approximately the same attenuation coefficient and speed of sound of other organs or tissues found in the human body. In the preferred embodiment the tissue equivalent material 35 mimics the tissue of the human liver and therefore optimally possesses an attenuation coefficient of 2.03 dB/cm at 3.5 MHz and a speed of sound of 1450 meters per second at 23° C. The preferred tissue equivalent material 35 is a type RB-143 elastomeric gel material manufactured by ATS Laboratories, Inc., in Bridgeport, Conn.

While the preferred phantom 10 is constructed so as to provide realistic images when used with an ultrasonic locating apparatus, it should be understood that X-ray locating equipment may also be used to locate the calculi.

In use, a fluid or gel (not illustrated) is poured into the phantom 10 through ports 16, thereby filling the gall bladder cavity 25, the kidney cavity 26, and the ducts 28–30. While distilled water is preferred, a low melting point elastomeric fluid may also be used provided that it remains liquid and can be drained from the cavities. The fluid or gel fills the organ cavities and supports an inserted concrement. The plugs 17 are then securely placed into ports 16 to prevent the fluid from escaping the phantom 10.

From the foregoing construction, it will be understood that the phantom 10 is constructed to accommodate at least two stones in the gallbladder cavity 25, each approximately 1.5 cm in diameter, one to be located in the anatomic neck and the other in the fundus, and at least two stones in the kidney cavity 26, one being about 5 by 7 mm in size in the proximal ureter and the other being 1.0 cm$^2$ in the renal pelvis.

The phantom 10 is constructed with conventional molding techniques which will be known to those skilled in the art. An elliptical mold simulating the human midsection is provided. Shapes corresponding to the gall bladder, kidney, and channels 20, 21, 22 are suspended on wires, above the mold, and the tissue equivalent material 35 is poured into mold and allowed to cool. As the material 35 reaches a predetermined point of congealing to sufficiently set around the shapes, the kidney, gall bladder, and channel shapes are pulled out, leaving cavities corresponding to the channels 20, 21, 22, gall bladder 25, kidney 26, and ducts 28–30.

In its intended use as a training device for location and destruction of calculi, the phantom 10 will be used in conjunction with a medical imaging or locating device and extracorporeal shock wave lithotripter. As described above, the gall bladder cavity 25, kidney cavity 26, and common bile duct 30 found in the phantom 10 emulate the size, shape and position of the organs and ducts found in the midsection of the human body. Before the trainee uses the phantom 10, a training supervisor first must decide the location and number of concrements 40 for placement in the phantom 10. After this decision is made, the supervisor removes the plugs 17 from the phantom 10, introduces a simulated concrement 40 such as a calcium carbonate ball or an actual surgical specimen into the gall bladder 25 and/or kidney 26 and/or common bile duct 30, and fills the channels 20, 21, 22, the gall bladder cavity 25, and the kidney cavity 26 with the fluid-like substance. The calculi may be placed in the cavities randomly, or may be guided with an instrument for placement in a particular region. The elongate portions 19 of the plugs 17 are then pushed into ports 16 to seal the ports. The phantom is then ready for use.

Typically, the phantom will be turned on its back 44 prior to use, so that it will simulate the torso of a reclining patient. While the phantom is moveable and durable, it is believed preferable to minimize movement of the phantom after placement of the concrements, so as to minimize likelihood that the concrements will move inside the phantom.

The trainee can now try his skill at locating the concrements 40 using a conventional ultrasonic locating apparatus or a conventional X-ray apparatus, and then fragmenting the concrements with a conventional ESWL. When an ultrasound device is used, ultrasonic coupling jelly is placed on the exterior surface of the phantom 10, typically along the front 43 which simulates the front abdomen. An ultrasound transducer (not shown) is moved around the exterior surface of the phantom 10 until the concrements are located.

FIG. 5 illustrates typical diagnostic ultrasonic images of the phantom 10 seen on a display screen 50 of a conventional ultrasonic location apparatus such as a model MPL 9000 integrated ultrasound imaging and ESWL apparatus manufactured by Dornier Medical Systems, Inc., Atlanta, Ga., the assignee of the present invention. These images are associated with the respectively numbered imaging vectors 5A–5D in FIGS. 1 and 6. As mention, the preferred ultrasound imaging apparatus is integrated with an ESWL, so that once concrements are located, the coordinates of the located concrements are automatically generated and utilized for aiming the shock waves generated by the ESWL.

Figure 5A:
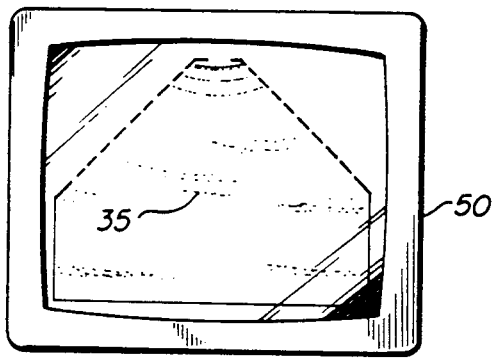
FIG. 5, consisting of FIGS. 5A–5D, are simulated ultrasonic images of cross sections of the preferred phantom of FIG. 1, viewed with an ultrasonic device positioned at the points 5A, 5B, 5C, and 5D, respectively, in FIG. 1.

FIG. 5A illustrates an image that should be recognized by the physician or technician as human liver tissue as the ultrasound transducer is positioned at the point 5A in FIGS. 1 and 5. It will be appreciated that in this view, no simulated organs (other than liver tissue) are within the path of the ultrasound beam, so no recognizable images are present.

Figure 5B:
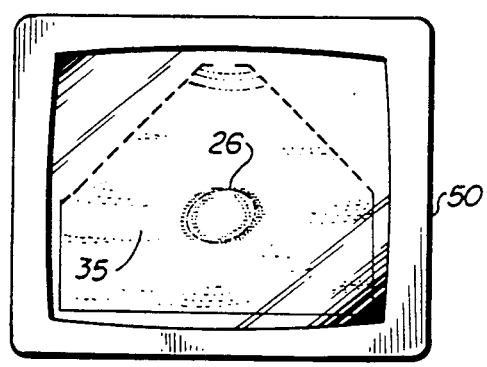
Figure 5C:
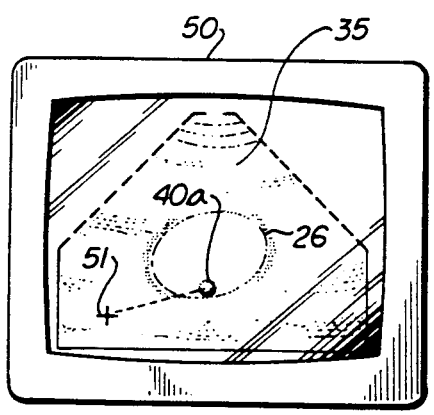

FIG. 5B illustrates the image seen as a portion of the kidney cavity 26 comes within the imaging beam. FIG. 5C illustrates the image of the kidney cavity 26 with a concrement 40a located in the interior of the kidney cavity.

Figure 5D:
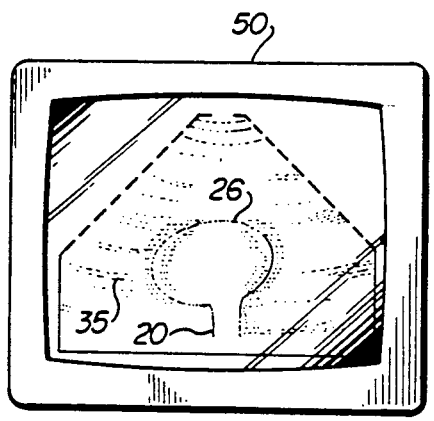

FIG. 5D illustrates the radiological image of the cross section of the kidney cavity 26 and the channel 20, which are clearly defined in the image and recognizable as such.

After the trainee locates the concrement 40a, as illustrated in FIG. 5C, it then remains to destroy the concrement. In applications involving the preferred Model MPL 9000 integrated ultrasound locating and ESWL apparatus described above, the coordinates of the concrement are automatically computed based on position transducer readings of the arm supporting the ultrasound transducer. The trainee merely moves a cursor 51 generated on the screen 50 by the system onto the located concrement 40a, and the coordinates of the concrement are automatically determined for use in aiming and focussing the associated ESWL. The trainee then focuses a shock wave on the concrement, causing fragmentation.

The foregoing procedure of imaging, location, and destruction is repeated until all the concrements 40 that were placed in the phantom 10 are fragmented. Plugs 17 are removed and the phantom 10 is inverted, thereby allowing the fluid like substance and fragments of the concrements 40 to exit the phantom. These fragments may then be inspected for determination of accuracy of aiming and effectiveness of the procedure.

More concrements 40 are now ready to be placed in the interior of the phantom 10. These locating and fragmenting procedures can be utilized on the phantom 10 an indefinite number of times, until the training supervisor is satisfied that the trainee physician or technician is now ready to perform the ultrasonic locating and ESWL procedures on live patients.

As shown in phantom in FIG. 2, a separate flushing duct 55 may be provided from any of the organ cavities 25, 26 to the top 12 of the phantom 10, with an associated plug (not shown), so as to facilitate the flushing-out of a fragmented concrement.

The preferred embodiment of the present invention has been disclosed by way of example and it will be understood that other modifications may occur to those skilled in the art without departing from the scope and the spirit of the appended claims.

What is claimed is:

1. A semi-anthropomorphic medical imaging training phantom, comprising:
   an opaque elastomeric mass;
   at least one cavity defined at a predetermined location within said mass, said cavity simulating a human organ; and
   a channel defined at a predetermined location for introducing a concrement into said cavity from outside said mass, said channel extending from said cavity to the exterior of said mass.

2. The phantom of claim 1, wherein said mass comprises a tissue equivalent material.

3. The phantom of claim 2, wherein said tissue equivalent material has an attenuation coefficient of about 2.03 dB/cm at 3.5 MHz, thereby mimicking human liver.

4. The phantom of claim 2, wherein said tissue equivalent material has a speed of sound of about 1450 meters per second at 23° C., thereby mimicking human liver.

5. The phantom of claim 1, wherein said mass is generally ellipsoid in shape.

6. The phantom of claim 5, wherein said ellipsoid mass has a flat top and a flat bottom.

7. The phantom of claim 1, wherein said channel means and said cavity means are filled with a fluid-like substance.

8. The phantom of claim 7, wherein said fluid-like substance comprises a tissue equivalent material having acoustic properties different from the acoustic properties of said mass.

9. The phantom of claim 7, wherein said fluid-like substance comprises an elastomeric material having a low melting point.

10. The phantom of claim 7, wherein said fluid-like substance is water.

11. The phantom of claim 7, further comprising means for closing said channel means, whereby said fluid-like substance is retained in said channel defining means and said cavity defining means.

12. The phantom of claim 1, wherein said simulated organ comprises a gallbladder.

13. The phantom of claim 1, wherein said simulated organ comprises a cystic or common bile duct.

14. The phantom of claim 1, wherein said simulated organ comprises a kidney.

15. The phantom of claim 14, further comprising simulated calyces molded in the interior of said kidney.

16. A semi-anthropomorphic medical imaging and ESWL training phantom, comprising:
   an opaque mass formed of an elastomeric tissue equivalent material;
   a plurality of cavities formed within said mass, said cavities positioned, sized and shaped in such a manner as to simulate the position, size and shape of at least a gallbladder and a human kidney found in the abdominal area of a human body;
   a plurality of channels formed within said mass at predetermined locations, one of said channels leading from said simulated kidney to the exterior of said phantom and the other said channel leading from said simulated gallbladder to the exterior of said phantom,
   whereby a technician can place at least one concrement into at least one of said cavities, locate, destroy and subsequently remove said concrement;
   a fluid-like substance filling said cavities; and
   means for sealing said channels, whereby said fluid-like substance is retained within said phantom during imaging and ESWL treatment of the phantom.

17. The phantom of claim 16, wherein said mass is ellipsoid in shape.

18. The phantom of claim 16, wherein said tissue equivalent material has an attenuation coefficient of about 2.03 dB/cm at 3.5 MHz, thereby mimicking human liver.

19. The phantom of claim 16, wherein said tissue equivalent material has a speed of sound of about 1450 meters per second at 23° C., thereby mimicking human liver.

20. The phantom of claim 16, wherein said fluid-like substance comprises a tissue equivalent material having different acoustic characteristics than said mass.

21. The phantom of claim 16, wherein said fluid-like substance is water.

22. The phantom of claim 16, wherein said sealing means comprises plugs extending from an exterior surface of said phantom to said cavities, thereby filling said channel means.

23. The phantom of claim 16, wherein said phantom comprises at least three cavities formed within said mass, for simulating the position, size and shape of a gallbladder, a human kidney, and a common bile duct.

24. A method for locating and fragmenting a concrement found at least one simulated organ, comprising the steps of:
   providing a semi-anthropomorphic phantom comprising an elastomeric mass having at least one simulated organ at a predetermined location on the interior of said mass;
   providing a channel at a predetermined location extending from said simulated organ to the exterior of said phantom;
   placing a concrement into said simulated organ through said channel;
   filling said simulated organ and said channel means with a fluid-like substance;
   sealing said channel with a closing means;
   locating said concrement with a locating apparatus; and
   destroying said concrement with a concrement destroying apparatus.

25. The method of claim 24, wherein said fluid-like substance comprises water.

26. The method of claim 24, wherein said fluid-like substance comprises an elastomeric gel having a low melting point.

27. The method of claim 24, wherein said locating apparatus comprises an ultrasonic locating apparatus.

28. The method of claim 24, wherein said locating apparatus comprises an X-ray locating apparatus.

29. The method of claim 24, wherein said concrement destroying apparatus comprises an extracorporeal shock wave lithotripter.

30. The method of claim 24, further comprising the steps of, after the step of destroying said concrement, releasing said closing means from said phantom, and removing the remains of said concrement to inspect the results of the method.

* * * * *